United States Patent
Lepage et al.

(10) Patent No.: US 9,556,378 B2
(45) Date of Patent: Jan. 31, 2017

(54) CHELATING AGENT PRECURSORS, FLUIDS CONTAINING THEM, AND THEIR USE

(75) Inventors: James N. Lepage, Chicago, IL (US); Cornelia Adriana De Wolf, Eerbeek (NL); Johanna Hendrika Bemelaar, Deventer (NL); Adrianus Maria Reichwein, Velp (NL); Axel Carstens, Kleve (DE); Edwin Rudolf Antony Bang, Arnhem (NL)

(73) Assignee: AKZO NOBEL CHEMICALS INTERNATIONAL B.V., Amersfoort (NL)

( * ) Notice: Subject to any disclaimer, the term of this patent is extended or adjusted under 35 U.S.C. 154(b) by 399 days.

(21) Appl. No.: 14/000,675

(22) PCT Filed: Feb. 20, 2012

(86) PCT No.: PCT/EP2012/052824
§ 371 (c)(1),
(2), (4) Date: Aug. 21, 2013

(87) PCT Pub. No.: WO2012/113738
PCT Pub. Date: Aug. 30, 2012

(65) Prior Publication Data
US 2013/0331304 A1 Dec. 12, 2013

Related U.S. Application Data

(60) Provisional application No. 61/445,291, filed on Feb. 22, 2011.

(30) Foreign Application Priority Data

Mar. 17, 2011 (EP) .................................. 11158650

(51) Int. Cl.
C09K 8/86 (2006.01)
C07C 227/18 (2006.01)
(Continued)

(52) U.S. Cl.
CPC .............. *C09K 8/86* (2013.01); *C07C 227/18* (2013.01); *C07C 229/12* (2013.01);
(Continued)

(58) Field of Classification Search
None
See application file for complete search history.

(56) References Cited

U.S. PATENT DOCUMENTS 5,190,782 A 3/1993 Yarger et al.
8,043,996 B2 10/2011 Harris
(Continued)

FOREIGN PATENT DOCUMENTS

DE 41 33 688 A1 4/1993
EP 0 959 092 A1 11/1999
(Continued)

OTHER PUBLICATIONS

English translation of JP11092436-A, Sep. 22, 1997.*
(Continued)

*Primary Examiner* — Jeffrey Washville
(74) *Attorney, Agent, or Firm* — Sandra B. Weiss

(57) ABSTRACT

The present invention relates to a chelating agent precursor that contains glutamic acid N,N-diacetic acid (GLDA) and/or methylglycine N,N-diacetic acid (MGDA) wherein at least one of the carboxylic acid groups is present as a carboxylic acid derivative selected from the group of amides, anhydrides, and esters, combinations thereof, and salts thereof, provided that it is not the triethyl ester of GLDA, the triethyl mono-t-butyl ester of GLDA, the tri-t-butyl ester of GLDA, the monobenzyl tri-t-butyl ester of GLDA, any ester or amide that contains azacycloalkane groups, any amide that contains biotin groups, any amide that contains minoethylcarbamoyl based amide groups, (S)-diethyl 2,2'-(1-benzyloxy)-1,5-dioxo-5-(prop-2-ynylamino)
(Continued)

Figure 1:
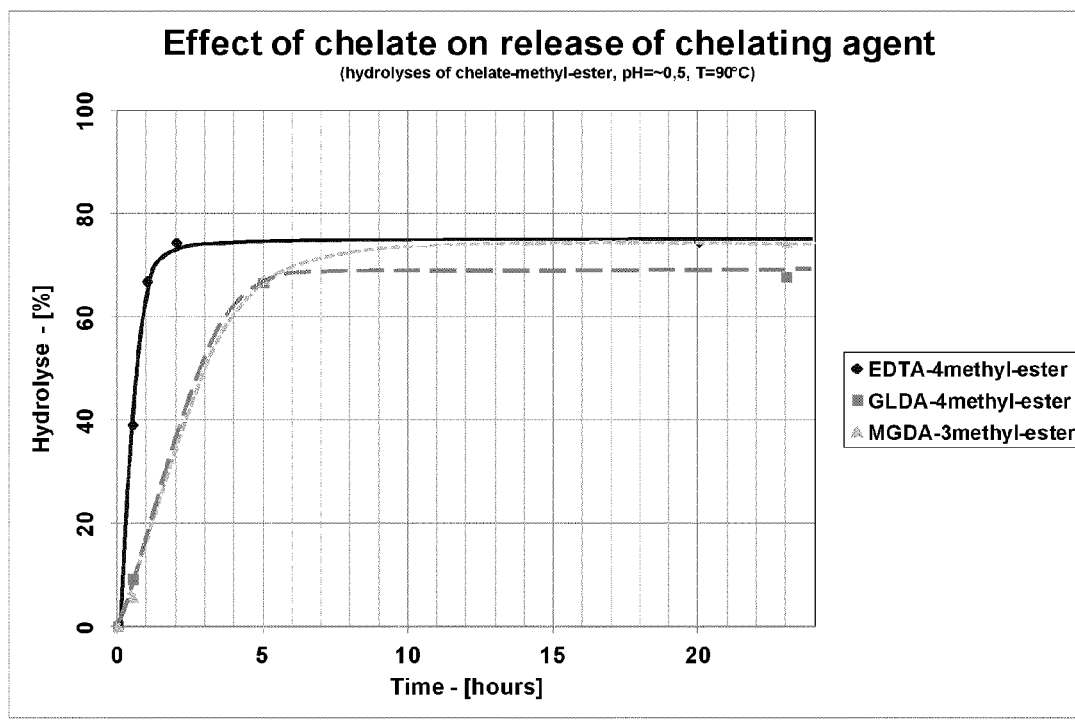

pentan-2-ylazanediyl-diacetate, diethyl 2,2'-(5-(3-azidopropylamino)-1-(benzyloxy)-1,5-dioxo-pentan-2-ylazanediyl-diacetate, the trimethyl ester of MGDA, the monomethyl ester dimethylamide of MGDA, the dibenzyl ester of MGDA, the dibenzyl mono t-butyl ester of MGDA, the di t-butyl ester of MGDA, the di-t-butyl-monobenzyl ester of MGDA, N,N-bis(benzyloxycarbonylmethyl)-N'-methoxycarbonyl-methyl-alanine amide, or N,N-bis(tert-butoxycarbonyl)-N'-methoxycarbonylmethyl-alanine amide, and esters of GLDA immobilized on a gel, and that the amide is not the amide of ammonia, to a fluid containing the above chelating precursor and a liquid, and to the use of a chelating agent precursor of MGDA and GLDA and fluids containing them in an application wherein delayed acidity or the chelating capacity is useful, such as in descaling, bleaching, cleaning, and treating oil and/or gas-containing subterranean formations.

13 Claims, 4 Drawing Sheets

(51) Int. Cl.
| | |
|---|---|
| C07C 229/12 | (2006.01) |
| C07C 229/24 | (2006.01) |
| C07C 231/02 | (2006.01) |
| C07C 237/06 | (2006.01) |
| C09K 8/528 | (2006.01) |

(52) U.S. Cl.
CPC .......... *C07C 229/24* (2013.01); *C07C 231/02* (2013.01); *C07C 237/06* (2013.01); *C09K 8/528* (2013.01)

(56) References Cited

U.S. PATENT DOCUMENTS

| | | | |
|---|---|---|---|
| 2003/0236430 A1 | 12/2003 | Allen et al. | |
| 2005/0014654 A1 | 1/2005 | Qu et al. | |
| 2005/0056423 A1 | 3/2005 | Todd et al. | |
| 2008/0197082 A1 | 8/2008 | Guzmann et al. | |

FOREIGN PATENT DOCUMENTS

| | | |
|---|---|---|
| JP | 50-53323 A | 5/1975 |
| JP | 55-47384 A | 4/1980 |
| JP | 59-149927 A | 8/1984 |
| JP | 1-165560 A | 6/1989 |
| JP | 10-231469 A | 9/1998 |
| JP | 2004-210812 A | 7/2004 |
| WO | WO 02/055843 A1 | 7/2002 |
| WO | WO 2004/087284 A1 | 10/2004 |
| WO | WO 2006/013042 A2 | 2/2006 |
| WO | WO 2006/134145 A1 | 10/2006 |
| WO | WO 2008/038033 A1 | 4/2008 |
| WO | WO 2008/139164 A1 | 11/2008 |
| WO | WO 2008/145609 A1 | 12/2008 |
| WO | WO 2009/024519 A1 | 2/2009 |
| WO | WO 2012/116032 A1 | 8/2012 |

OTHER PUBLICATIONS

Grauer et al., "Synthetic Receptors for the Differentiation of Phosphorylated Peptides with Nanomolar Affinities," w-supporting Info, Chem. Eur. J. (2008), 14, pp. 8922-8927.

Grote et al., "Stereocontrolled Synthesis of DTPA Analogues Branched in the Ethylene Unit," J. Org. Chem., 1995, 60, pp. 6987-6997.

Lata et al., "High-Affinity Adaptors for Switchable Recognition of Histidine-Tagged Proteins," J. Am. Chem. Soc., 2005, 127, pp. 10205-10215.

Liu et al., "Convergent and Sequential Synthesis of Dendritic, Multivalent Complexing Agents," Synthesis 2002, No. 10, pp. 1398-1406.

Ohtani et al., "Five-Coordinated Complexes Containing an Optically Active Ligand," Chemistry Letters (1980), pp. 465-466.

Stadlbauer et al., "Utilizing Reversible Copper(II) Peptide Coordination in a Sequence-Selective Luminescent Receptor," Chem. Eur. J. 2008, 14, pp. 2536-2541.

English language abstract of JP 10-231469 A published Sep. 2, 1998.

English language abstract of JP 2004-210812 A published Jul. 29, 2004.

European Search Report dated Jul. 4, 2011 for related Application No. 11158650.9.

International Search Report and Written Opinion dated Mar. 26, 2012 for related International Application No. PCT/EP2012/052824.

English language abstract of JP 50-53323 A published May 12, 1975.

English language abstract of JP 55-47384 A published Apr. 3, 1980.
English language abstract of JP 59-149927 A published Aug. 28, 1984.

English language abstract of JP 1-165560 A published Jun. 29, 1989.
English language translation of DE 41 33 688 A1 published Apr. 15, 1993.

English language translation of EP 0 959 092 A1 published Nov. 24, 1999.

Collins et al., SPE 140816, "A Biodegradable Chelating Agent Designed to be an Environmentally Friendly Filter-cake Breaker," Society of Petroleum Engineers (2011) pp. 1-10.

Drakopoulou et al., "Design and synthesis of multifunctional phospholipids," Tetrahedron Letters 41 (2000) pp. 4131-4134.

\* cited by examiner

CHELATING AGENT PRECURSORS, FLUIDS CONTAINING THEM, AND THEIR USE

This application is the U.S. National Phase of PCT/EP2012/052824 filed on Feb. 20, 2012 and claims the benefit of U.S. Provisional Application No. 61/445,291 filed on Feb. 22, 2011 and European Application No. 11158650.9 filed on Mar. 17, 2011, the contents of each of which are incorporated herein by reference.

The present invention relates to solutions/fluids having a delayed acidity and chelating capacity which contain a precursor of the chelating agents glutamic acid N,N-diacetic acid (GLDA) and/or methylglycine N,N-diacetic acid (MGDA), to the chelating agent precursors, and to the use of both the fluids and the chelating agent precursors.

Solutions containing a precursor of an aminopolycarboxylic acid that have a delayed acidity and chelating capacity as a result are known in the art. US 2005/0056423 discloses fluids suitable for removing filter cakes that contain a carboxylic acid ester and a base capable of catalyzing the hydrolysis of this ester. The ester is said to be chosen from the group of several esters of ethylenediamine tetra acetic acid.

However, there is a need in the art for improved fluids providing a delayed acidity and chelating capacity which have a different hydrolysis profile.

It has now been found that precursors of GLDA or MGDA wherein at least one of the carboxylic acid groups is an ester, anhydride or amide instead of a carboxylic acid or carboxylate group have a different hydrolysis profile from the esters known in the art and at the same time show a favourable anti-corrosive profile. With the present invention it has additionally been found possible to prepare tailored molecules for a particular application in which a controlled release of the chelating agent is desirable. Finally, the molecules with which the chelating agent is reacted to give the ester, anhydride, or amide—being an alcohol, carboxylic acid or amine, respectively—can be chosen in such a way that functional compounds can be added to a fluid for a particular purpose.

Accordingly, the present invention provides chelating agent precursors of the chelating agents glutamic acid N,N-diacetic acid (GLDA) and/or methylglycine N, N-diacetic acid (MGDA) wherein at least one of the carboxylic acid groups is present as a carboxylic acid derivative selected from the group of amides, anhydrides, and esters, combinations thereof, and salts thereof, provided that it is not the triethyl ester of GLDA, the triethyl mono-t-butyl ester of GLDA, the tri-t-butyl ester of GLDA, the monobenzyl tri-t-butyl ester of GLDA, any ester or amide that contains azacycloalkane groups, any amide that contains biotin groups, any amide that contains aminoethylcarbamoyl based amide groups, (S)-diethyl 2,2'-(1-benzyloxy)-1,5-dioxo-5-(prop-2-ynylamino)pentan-2-ylazanediyl-diacetate, diethyl 2,2'-(5-(3-azidopropylamino)-1-(benzyloxy)-1,5-dioxo-pentan-2-ylazanediyl-diacetate, the trimethyl ester of MGDA, the monomethyl ester dimethylamide of MGDA, the dibenzyl ester of MGDA, the dibenzyl mono t-butyl ester of MGDA, the di t-butyl ester of MGDA, the di-t-butyl-monobenzyl ester of MGDA, N,N-bis(benzyloxy-carbonylmethyl)-N'-methoxycarbonylmethyl-alanine amide or N,N-bis(tert-butoxy-carbonyl)-N'-methoxycarbonylmethyl-alanine amide, and esters of GLDA immobilized on a gel, and that the amide is not the amide of ammonia.

The present invention particularly excludes the MGDA and GLDA esters and amides described in prior art documents, such being the triethyl ester of GLDA, triethyl mono-t-butyl ester of GLDA, tri-t-butyl ester of GLDA, monobenzyl tri-t-butyl ester of GLDA, as disclosed in WO 2004/087284, WO 2006/013042, WO 2008/145609, and S. Lata et al. in "High-affinity Adaptors for switchable recognition of histidine-tagged proteins," *JACS*, Vol. 127, No. 29, 2005, pp. 10205-10215; any ester or amide that contains azacycloalkane groups, like e.g. tetraazacyclododecane groups as e.g. disclosed in A. Grauer et al. in "Synthetic receptors for the differentiation of phosphorylated peptide with nanomolar affinities," *Chemistry a European Journal* Vol. 14, No. 29, Oct. 10, 2008, pp. 8922-8927, C. Liu, et al. in "Convergent and Sequential Synthesis of Dendritic, Multivalent Complexing Agents" in *Synthesis* 2002, No. 10, pp. 1398-1406, S. Lata et al. in "High-affinity Adaptors for switchable recognition of histidine-tagged proteins," *JACS*, Vol. 127, No. 29, 2005, pp. 10205-10215, WO2008/145609 or WO 2006/013042; any amide that contains biotin groups as e.g. disclosed in E. Drakopoulou et al. in "Design and synthesis of multifunctional phospholipids," *Tetrahedron Letters* 41 (2000) pp. 4131-4143; any amide that contains aminoethylcarbamoyl based amide groups, the (S)-diethyl 2,2'-(1-benzyloxy)-1,5-dioxo-5-(prop-2-ynylamino)pentan-2-ylazanediyl-diacetate, diethyl 2,2'-(5-(3-azidopropylamino)-1-(benzyloxy)-1,5-dioxo-pentan-2-ylazanediyl-diacetate esters of GLDA disclosed by Grauer et al in "Synthetic receptors for the differentiation of phosphorylated peptide with nanomolar affinities," *Chemistry a European Journal* Vol. 14, No. 29, Oct. 10, 2008, pp. 8922-8927; the trimethyl ester of MGDA and the monomethyl ester dimethylamide of MGDA disclosed by Ohtani et al. in "Five-coordinated complexes containing an optically active ligand," *Chemistry Letters,* Chemical Society of Japan, Jan. 1, 1980, pp. 465, 466; the dibenzyl ester of MGDA, the dibenzyl mono t-butyl ester of MGDA, di t-butyl ester of MGDA and the di-t-butyl-monobenzyl ester of MGDA, N,N-bis(benzyloxycarbonylmethyl)-N'-methoxycarbonylmethyl-alanine amide or N,N-bis(tert-butoxycarbonyl)-N'-methoxycarbonylmethyl-alanine amide as disclosed in C. W. Grote et al. in "Stereocontrolled Synthesis of DTPA analogues branched in the ethylene unit," *Journal of Organic Chemistry*, Am Chem Soc, Vol. 60, No. 21, Jan. 1, 1995; and esters of GLDA immobilized on a gel such as disclosed in WO 2004/087284.

In none of the above-described prior art documents are the GLDA and MGDA esters and amides as disclosed acknowledged to have a beneficial use as precursors for GLDA and MGDA; they are either disclosed as an intermediate in a synthesis route or as having benefits in completely different areas, like as peptide or protein receptors.

Finally, it should be understood that present invention does not cover the amide of GLDA and/or MGDA with ammonia.

In addition, the present invention provides fluids containing the above GLDA and/or MGDA amide, ester and/or anhydride and a liquid, wherein the liquid is preferably an aqueous liquid. Fluids are meant to include solutions, suspension, and emulsions; preferably, they are solutions.

Finally, the present invention relates to the use of chelating agent precursors selected from the group of GLDA esters, amides, and anhydrides and MGDA amides, esters, and anhydrides (i.e. GLDA and MGDA precursors) or fluids containing one or more of these precursors in applications wherein a delayed acidity and/or chelating capacity is desirable, such as in descaling, bleaching, cleaning, and treating oil and/or gas-containing subterranean formations.

It should be noted that WO 2009/024519 discloses the use of GLDA amides, wherein the amide is the amide that can be prepared by the reaction of one or more of the carboxylic acid groups with ammonia, in oil field applications and discloses that these GLDA amides can be hydrolyzed to GLDA. However, the use in oil field applications is mentioned within a long list of uses and not exemplified, nor are the benefits of using an amide in said particular application given. The amide of GLDA or MGDA obtainable from reaction of GLDA or MGDA with ammonia will not have a particular advantage in several applications as during hydrolysis of such precursors ammonia would be liberated which can be a nutrient for undesirable microorganisms, therefore, these amides are less preferred.

The precursors of GLDA or MGDA wherein at least one of the carboxylic acid groups is an ester, anhydride or amide instead of a carboxylic acid or carboxylate group do indeed have a different hydrolysis profile from the esters known in the art. First, both MGDA and GLDA are molecules with carboxylic acid groups that are chemically different, whereas in EDTA all carboxylic acid groups are the same. In consequence, the hydrolysis of MGDA and GLDA precursors is more differentiated and slower than that of EDTA precursors under the same conditions. Besides, compared to the state of the art EDTA esters, many GLDA esters were found to be liquids with a sufficient low viscosity and with a higher density than water. This leads to several advantages. First, it means that they can be pumped into subterranean formations. If they are pumped in an aqueous fluid they will sink to the bottom part of this aqueous fluid to act in the formation, where they are slowly hydrolyzed to the acidic GLDA molecule and the alcohol. In addition, the present invention also provides the amides and anhydrides of the chelating agents MGDA and GLDA, which have another hydrolysis profile than esters do, making it possible for a tailored molecule for a particular application to be made. Generally, anhydrides tend to be easier to hydrolyze than esters and amides are often more difficult to hydrolyze than esters, though of course the exact hydrolysis profile will depend on the specific choice of the alcohol, amine and/or carboxylic acid present within the GLDA and/or MGDA precursor. Therefore, depending on how much delay in releasing the acidity and the chelating capacity is desired, the best choice in molecule design can be made. Another advantage over EDTA esters is that the chelating agent precursors of the present invention can be more easily hydrolyzed under acidic conditions, as EDTA (as well as NTA) in its acidic form is hardly soluble in an aqueous fluid and will give undesired precipitation. Finally, the molecules within the chelating agent precursor to give the ester, anhydride, or amide—being the alcohol, carboxylic acid or amine, respectively—can be chosen in such a way that for a particular purpose functional compounds can be added which are released in the hydrolysis step together with the GLDA and/or MGDA.

The term treating oil and/or gas-containing subterranean formations in this application is meant to cover any treatment of the formation. It specifically covers treating the formation to achieve at least one of (i) an increased permeability, (ii) the removal of small particles, and (iii) the removal of inorganic scale, and so enhance the well performance and enable an increased production/recovery of oil and/or gas from the formation. At the same time it may cover cleaning the wellbore and descaling of the oil/gas production well and production equipment up to and including the oil refinery. The use of the chelating agent precursors in treating subterranean formations is particularly beneficial, as especially in this use it is beneficial to achieve a delayed availability of chemicals, like the chelating agent and the alcohol, amine or carboxylic acid, so that they will act more deeply in the formation and are not spent in a too early phase of the treatment process. Besides, a slow release especially in treating subterranean formations is advantageous, as it has been found that a slow dissolution of components of a formation (often carbonates) gives the best permeability improvement without damaging the formation. Accordingly, the present invention specifically covers a process of treating a subterranean formation wherein a chelating agent precursor of GLDA or MGDA or a fluid containing such a chelating agent precursor is introduced into the formation.

In this process the chelating agent precursor may be at least partly hydrolyzed when it is introduced into the formation or thereafter, during the treatment of the formation.

Even more preferably the present invention covers the use of the chelating agent precursor wherein the chelating agent precursor carboxylic acid derivative is an ester from a C1-C6 alcohol or a C1-C6 glycol, in treating a subterranean formation wherein the chelating agent precursor is at least partly hydrolyzed in the formation and the alcohol or glycol is released and in embodiments assists in hydrate inhibition and/or acts as a mutual solvent.

In another embodiment in the process to treat the formation, the fluid in addition contains an agent that assists in the hydrolysis of the chelating agent precursor to release GLDA and/or MGDA, such as an enzyme, a base or an acid.

Preferably in the treatment of a subterranean formation the chelating agent precursor is an ester of GLDA, even more preferably an ester of GLDA with a C1-C6 alcohol or a C1-C6 glycol, most preferably ester of GLDA with a C2-C6 alcohol or a C2-C6 glycol.

In embodiments of the process to treat a subterranean formation the pH of the fluid containing the chelating agent precursor is preferably between 1 and 7 and in another embodiment the subterranean formation is contacted with the fluid at a temperature of preferably between 25° C. and 204° C., even more preferably between 25 and 149° C., most preferably between 65 and 149° C.

In the embodiments wherein the chelating agent precursor of the present invention contains one or more ester groups, these ester groups may be derived from the reaction of GLDA and/or MGDA with an alcohol. This alcohol may contain one or more further groups like aromatic groups, amine groups, ether groups, ester groups, phosphorus-containing groups, sulfur-containing groups, amide groups, and hydroxyl groups. Preferably, the alcohol is an aliphatic alcohol containing 1 to 12 carbon atoms that optionally may contain additional hydroxyl, amine and/or ether groups. In yet another preferred embodiment, the alcohol contains a primary or secondary hydroxyl group. Even more preferably, the alcohol is chosen from the group of lower alcohols such as methanol, ethanol, propanol, butanol, pentanol, hexanol, heptanol, octanol, nonanol, decanol that may be linear or branched; glycols such as ethylene glycol, propylene glycol, diethylene glycol, dipropylene glycol, ethylene glycol mono butyl ether (EGMBE), neopentyl glycol, polyethylene glycol, polypropylene glycol, polyethylene glycol and polypropylene glycol based copolymers, and the like, and glycol ethers such as 2-methoxyethanol, diethylene glycol monomethyl ether; glycerol, hydroxypropanol, pentaerythritol, 1,1,1-trimethylol propane, 1,1,1-trimethylol ethane, 1,2,3-trimethylol propane, di-trimethylolpropane, di-pentaerythritol, 2-butyl-2-ethyl-1,3-propane diol, 1,6-hexane diol, cyclohexane dimethanol; lower amino alcohols such as aminoethanol, aminopropanol, aminobutanol; alkoxylated alcohols, preferably ethoxylated alcohols.

Mixed esters are also covered by the invention, i.e. esters of MGDA and/or GLDA with two or more different alcohols.

In the embodiments wherein the chelating agent precursor of the present invention contains one or more amide groups, these amide groups may be derived from the reaction of GLDA and/or MGDA with an amine. This amine may contain one or more further groups like aromatic groups, amine groups, ether groups, ester groups, amide groups, phosphorus-containing groups, sulfur-containing groups, and hydroxyl groups. Preferably, the amine is an aliphatic amine containing 1 to 12 carbon atoms that optionally may contain additional hydroxyl, carboxylic acid, amine and/or ether groups. In yet another preferred embodiment, the amine contains a primary or secondary amino group. Even more preferably, the amine is chosen from the group of lower amines such as aminomethane, aminoethane, aminopropane, aminobutane, aminopentane, aminohexane, aminoheptane, aminooctane, aminononane, aminodecane that may be linear or branched; lower amino alcohols such as aminoethanol, aminopropanol, aminobutanol; alkoxylated amines, preferably ethoxylated amines; amino acids that are well known to the person skilled in the art, such as the natural amino acids.

Mixed amides are also covered by the invention, i.e. amides of MGDA and/or GLDA with two or more different amines.

In the embodiments wherein the chelating agent precursor of the present invention contains one or more anhydride groups, these anhydride groups may be derived from the reaction of GLDA and/or MGDA with a carboxylic acid. This carboxylic acid may contain one or more further groups like aromatic groups, amine groups, ether groups, ester groups, amide groups, phosphorus-containing groups, sulfur-containing groups, and hydroxyl groups.

Preferably, the carboxylic acid is a fatty acid, or an aliphatic carboxylic acid containing 1 to 12 carbon atoms that optionally may contain additional hydroxyl, amine, carboxylic acid and/or ether groups. Even more preferably, the carboxylic acid is chosen from the group of lower carboxylic acids such as formic acid, acetic acid, propanoic acid, butanoic acid, pentanoic acid, hexanoic acid, heptanoic acid, octanoic acid, nonanoic acid, decanoic acid that may be linear or branched, glycolic acid; from the group of fatty acids that are well known to the person skilled in the art, such as lauric acid, myristic acid, palmitic acid, stearic acid, arachidic acid, oleic acid, oleinic acid, linoleic acid, α-linoleic acid, γ-linoleic acid, myristoleic acid, arachidonic acid, sapienic acid, erucic acid, palmitoleic acid, gadoleic acid, cetoleic acid, undecylenic acid, punicic acid, or a fatty acid derived from rapeseed oil, castor oil, safflower oil, linseed oil, soybean oil, sesame oil, poppyseed oil, perilla oil, hempseed oil, grapeseed oil, sunflower oil, maize oil, tall oil, whale oil, hevea oil, tung oil, walnut oil, peanut oil, canola oil, cottonseed oil, sugarcane fatty acid.

Mixed anhydrides are also covered by the invention, i.e. anhydrides of MGDA and/or GLDA with two or more different carboxylic acids.

In addition, the present invention covers chelating agent precursors of MGDA and/or GLDA in which the several groups are combined, i.e. containing not only ester, amide or anhydride groups but containing a mixture of two or more of them. For ease of manufacturing, however, chelating agent precursors in which the carboxylic acid/carboxylate groups are converted to the same ester, anhydride or amide group are preferred.

It is understood that by choosing the right functional compounds the physical properties, such as visco-elasticity, viscosity, and thermal stability, can be tailored to meet the requirements of the application.

Preferably the present invention relates to GLDA esters, even more preferably the lower GLDA esters (i.e. esters of GLDA with C1-C6 alcohols or glycols), most preferably esters of GLDA with C2-C6 alcohols or glycols, as these were found to be liquids having a low enough viscosity to pump them and due to their low water solubility to give a slow hydrolysis in water and a good oil compatibility.

The lower alcohols and glycols, especially the glycols (i.e. the C1-C6 glycols) are also preferred, as they have the advantage after hydrolysis of being mutual solvents, which is an advantage when using the chelating agent precursors in treating subterranean formations. A mutual solvent is a chemical additive regularly used in subterranean formation treatments that is soluble in oil, water, and acid-based treatment fluids. Mutual solvents are routinely used in a range of applications, such as removing heavy hydrocarbon deposits, controlling the wettability of contact surfaces before, during or after a treatment, and preventing or breaking emulsions as they increase the compatibility between hydrophobic and hydrophilic materials. A commonly used mutual solvent is ethyleneglycolmonobutyl ether, generally known as EGMBE. The lower alcohols and glycols (C1-C6 alcohols and C1-C6 glycols, like methanol, ethanol, monoethylene glycol, diethylene glycol, triethylene glycol) are also preferred, as they can be used as hydrate inhibitors. Gas hydrates are ice-like clathrate solids that are formed from water and small hydrocarbons at elevated pressures and lower temperatures in oil or gas production operations (i.e. treatments of subterranean formations). The temperature below which hydrates can be formed increases with increasing pressure and can be a high as 25-30° C. Gas hydrates are most commonly encountered in subsea or cold climate wet gas or multi-phase (oil/water/gas) pipelines, where they can block the flow of fluids, but they can also be formed during drilling, completion, and workover operations, as well as in gas-processing facilities, gas injection lines, and aqueous chemical injection in gas lift lines if the pressure-temperature conditions are right. Lower alcohols and glycols act as thermodynamic hydrate inhibitors and are by far the most common chemicals class used to prevent hydrate formation. They work by changing the bulk thermodynamic properties of the fluid system, thereby shifting the equilibrium conditions for gas hydrate formation to lower temperatures or higher pressures. Thus they can be used to prevent hydrate formation and also to "melt" existing hydrate deposits.

In another embodiment the alkoxylated alcohol and alkoxylated amines are preferred, as they have the advantage of being able to function as surfactants. Amines are known to often have an anticorrosive action and are preferred for this reason.

The carboxylic acids are preferred, as they provide the solution with additional acidity after hydrolysis of the anhydride.

In addition, many alcohols have a biocidal activity and therefore they can improve the biocidal activity of the fluid after hydrolysis, e.g. in sanitizing formulations or formulations to control the sulfate-reducing bacteria in subterranean formations.

EXAMPLES

Example 1

Preparation of GLDA Ethyl Esters

In the examples glutamic acid N,N-diacetic acid and ethylene diamine tetraacetic acid were obtained from Akzo Nobel Functional Chemicals BV (Dissolvine 8 product line) and methylglycine N,N-diacetic acid was obtained from BASF Corporation (Trilon M® product line).

Example 1a

GLDA Mono Ethyl Ester

A slurry of glutamic acid N,N-diacetic acid and a catalytic amount of sulfuric acid in ethanol was refluxed for 1 hour. After removal of the ethanol by evaporation a white solid remained. According to the $^1$H NMR, the product had a GLDA:ethyl ester ratio of 1:1.

The formed product has a pH of 1.8 (1 wt % in water)

Example 1b

GLDA Tetra Ethyl Ester 4.4 eq $SOCl_2$ was added slowly to a slurry of 1 eq glutamic acid N,N-diacetic acid in ethanol. After all $SOCl_2$ had been added, the mixture was refluxed for 1 hour and all ethanol was removed, together with the excess amount of HCl. A milk-like substance remained, which was analyzed by $^1$H NMR to be GLDA tetra ethyl ester. The pH of a 1% slurry in water is 1.8.

By adding a fresh amount of ethanol to the product, together with 1 eq $Na_2CO_3$, a less acidic tetraethyl ester product could be made. The mixture was stirred overnight, filtrated, and the ethanol removed. To remove all carbonate, ether was added and after filtration the ether was evaporated. The resulting liquid was established by $^1$H NMR to be GLDA tetraethyl ester, with a pH of ~9 as a 1% slurry in water.

Example 2

Preparation of a Range of GLDA, MGDA, and EDTA Esters

A range of chelating agent esters is synthesized using the thionyl chloride ($SOCl_2$) route of Example 1 b again. The following equation shows the simplified esterfication reaction

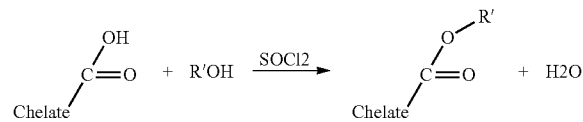

The chelate esters were prepared according to the following general method. The intake of the reactant for the preparation of the specific chelate esters is listed in Table 1.

The solid chelate acid was placed in a round bottom flask with 2 side necks equipped with a cooler and a dropping funnel. The alcohol or glycol was added in a molar excess and a slurry was formed. The slurry was stirred with an oval magnetic stirring bar. An excess 0.5 equivalent $SOCl_2$ compared to total equivalent carboxyl groups of the chelating agent, i.e. 4 carboxyl groups for GLDA or 3 for MGDA, was added very slowly to the slurry with a dropping funnel because of the violent reaction.

TABLE 1 intake amounts for synthesis of the esters

| | MeOH/1-propanol/ 1-butanol/EGMBE [g] | chelate in acid form [g] | SOCl2 [g] |
|---|---|---|---|
| GLDA 4 methyl ester | ~100 | 12.5 | 25.4 |
| GLDA 4 propyl ester | ~100 | 12.9 | 26.3 |
| GLDA 4 butyl ester | ~150 | 11 | 22.4 |
| GLDA 4 EGMBE | ~150 | 12 | 24.4 |
| EDTA 4 methyl ester | ~100 | 10.2 | 18.7 |
| EDTA 4 propyl ester | ~100 | 12.7 | 23.3 |
| EDTA 4 butyl ester | ~150 | 12.9 | 23.6 |
| MGDA 3 methyl ester | ~100 | 9.3 | 18.9 |

Next, the mixture was refluxed until the solids were dissolved, after which the solution was refluxed for 1 additional hour. Total reflux time was between 2 and 7 hours depending on the size of the alcohol chain. For example, methanol required a reflux time of 2 hours and butanol was refluxed during 7 hours. Subsequently, the solution was cooled down and the alcohol or glycol was evaporated with a rotavap at ~20 mBar. Next the flask was placed in a stove at 40° C. at ~1 mBar for 24 hours to remove the remaining volatiles.

In total, eight different chelate esters were synthesized and their hydrolysis properties examined under oil field conditions:

GLDA-tetramethyl ester of methanol and GLDA-$H_4$
GLDA-tetrapropyl ester of 1-propanol and GLDA-$H_4$
GLDA-tetrabutyl ester of 1-butanol and GLDA-$H_4$
GLDA-tetraEMGBE ester of EMGBE (ethylene mono glycol butyl ether) and GLDA-$H_4$
EDTA-tetraethyl ester of methanol and EDTA-$H_4$
EDTA-tetrapropyl ester of 1-propanol and EDTA-$H_4$
EDTA-tetrabutyl ester of 1-butanol and EDTA-$H_4$
MGDA-trimethyl ester of methanol and MGDA-$H_4$ The purity of the esters as given in Table 2 was determined by $^1$H and $^{13}$C-NMR. Besides, a visual observation was carried out to determine the initial state of the ester such as colour, liquid/solid.

In addition, where possible, the following physical properties of the chelate esters were determined at 25° C.:

Viscosity in mPas
Surface tension in mN/m
Density in kg/m$^3$

The viscosity was determined with a Brookfield DV-II viscometer equipped with spindle 25, which is suitable to measure high-viscous liquids. The principle of operation of the DV-II is to drive a specific spindle which is immersed in the test fluid. The viscous drag of the fluid against the spindle is measured by a calibrated spring. The viscosity is calculated from the rotational speed, type, and the torque of the spindle. In addition, the surface tension was determined with a bubble pressure tensiometer. The tensiometer produces gas bubbles at a constant rate and blows them through a capillary which is submerged in the sample liquid. The pressure (P) inside of the bubble continues to increase and the maximum value is obtained when the bubble has the completely hemispherical shape whose radius corresponds exactly to the radius of the capillary.

By following each step of the bubble formation, change of bubble radius, and the corresponding pressure, the dynamic surface tension can be determined using the Laplace equation in the reduced form for spherical bubble shape within the liquid, equation:

$$\sigma = (\Delta P_{max} \cdot R_{cap})/2$$

where:
σ=dynamic surface tension
ΔPmax=maximum pressure drop
Rcap=radius of capillary The density was determined gravimetrically by slowly sucking up exactly 0.50 ml of the chelate ester in a weighted pipette and by weighing the total weight of the pipette and the chelate-ester, the weight of 0.50 ml of chelate ester could be determined.

In the following Table 2 the results of the visual observation and the measurement of the physical properties of the synthesized esters are shown.

TABLE 2 properties of the synthesized esters

| | initial state of ester [—] | Viscosity [mPas] | color [—] | Purity [%] | Surface tension [mN/m] | Density [kg/m3] |
|---|---|---|---|---|---|---|
| GLDA 4 methyl ester | sticky resin like | n.p. | white | 80 | n.p. | — |
| GLDA 4 propyl ester | Liquid | 178 | light yellow | 95 | 69.2 | 1.11 |
| GLDA 4 butyl ester | Liquid | 38 | light yellow | 95 | 41.3 | 1.04 |
| GLDA 4 EGMBE | Liquid | 67 | brown | 90 | 47.8 | 1.06 |
| EDTA 4 methyl ester | sticky crystals | n.p. | white | 95 | n.p. | — |
| EDTA 4 propyl ester | Liquid | 260,000 | light yellow | 92 | 51.3 | >1 |
| EDTA 4 butyl ester | Liquid | 8,100 | brown | 85 | 52.6 | >1 |
| MGDA 3 methyl ester | sticky resin-like | n.p. | white | 85 | n.p. | — | n.p. = not possible to determine.

The density of EDTA-tetrapropyl and butyl ester could not be measured because of the high viscosity; however, the density was clearly higher than water All chelate methyl esters were sticky and not easy to handle and EDTA-tetramethyl ester behaved even more like a solid. All methyl esters dissolved easily compared to the butyl esters, which are insoluble in water. The propyl, butyl, and EMGBE chelate esters behaved more like a liquid. The butyl esters of EDTA and GLDA at low pH show two phases, an organic and an aqueous phase. Surprisingly, all the GLDA esters except for the methyl ester show an extremely clear two-phase system in an aqueous environment, while the EDTA esters are more easily emulsified in the water layer if the bottles are vigorously shaken. In contrast, the GLDA layer stays intact. In addition, there is a remarkable difference between the viscosity of GLDA ester and EDTA ester with comparable ester groups; GLDA ester behaves much more like a nicely flowing fluid than EDTA ester. This relatively low viscosity of GLDA esters is a big advantage in handling, as it can easily be pumped into the formation.

The specific weights or densities of all chelate esters were above the specific weight of water, which implies that the heavier chelate ester will sink, which can be an advantage in for example an oil well, as the fluid will more easily reach the target zone. Especially the GLDA ester showed this advantage.

An overview of the differences in physical state is given in Table 3.

TABLE 3

Solubility of chelate ester in water

| | Soluble in water (pH = 0.5) [—] | Soluble in water (pH = ~7) [—] |
|---|---|---|
| GLDA 4 methyl ester | Yes | — |
| GLDA 4 propyl ester | no (2 phases) | no (2 phases) |
| GLDA 4 butyl ester | no (2 phases) | — |
| GLDA 4 EGMBE | no (2 phases) | — |
| EDTA 4 methyl ester | Yes | Yes |
| EDTA 4 propyl ester | Yes | no (2 phases) |
| EDTA 4 butyl ester | no (2 phases) | — |
| MGDA 3 methyl ester | Yes | — |

Example 3

Hydrolysis of the Chelate Esters

In several experiments the hydrolysis of the chelate esters of Example 2 was investigated. First, the hydrolysis rate of the chelate esters was determined with $^1$H and $^{13}$C-NMR. NMR results showed that the hydrolysis of GLDA and MGDA methyl esters can be interpreted as slow-releasable. These chelate esters demonstrated an almost complete hydrolysis after ~2 days at 70° C. Secondly, the hydrolysis rate was followed by determination of the Fe-TSV, which gives the concentration of the released chelate acid. To determine the Fe-TSV the chelate ester was added to demi water in a 5 ml glass vial, resulting in an ester concentration of 20 wt %. The mixture was continuously homogenized by shaking and a treatment in the ultrasonic bath. Subsequently, the vial was placed in a stove at 90° C. to simulate well conditions. After certain time intervals a sample was taken and analyzed on Fe-TSV. The percentage of hydrolysis is defined by:

$$\frac{FeTSV \text{ measured}}{c \mid calculated \text{ chelate concentration at start}} * 100\%$$

The calculated chelate concentration at the start is calculated from the intake of the ester. The value is corrected for the purity as measured by NMR, assuming a 100% conversion of the corresponding chelate.

Example 3a

Effect of Chelating Agent on Hydrolysis

The results of the rate of hydrolysis of the chelate esters with methyl groups are demonstrated in FIG. 1. It is clearly seen that the EDTA-methyl ester is hydrolyzed much faster than the corresponding GLDA or MGDA-methyl ester. Also it was found that GLDA-tetramethyl esters and MGDA-trimethyl esters have nearly the same speed of hydrolysis. However, MGDA only releases 3 methanol groups, whereas GLDA can release 4 methanol groups in the same time frame. The higher methanol concentration might constitute a more effective way to prevent hydrate formation.

It is important to note that solid EDTA is formed when hydrolyzing the EDTA esters. Apparently the solubility limit of ETDA acid is reached. GLDA and MGDA do not suffer from this disadvantage, as the solubility of GLDA and MGDA acid is significantly higher.

Example 3b

Effect of Alcohol on Hydrolysis

Figure 2:
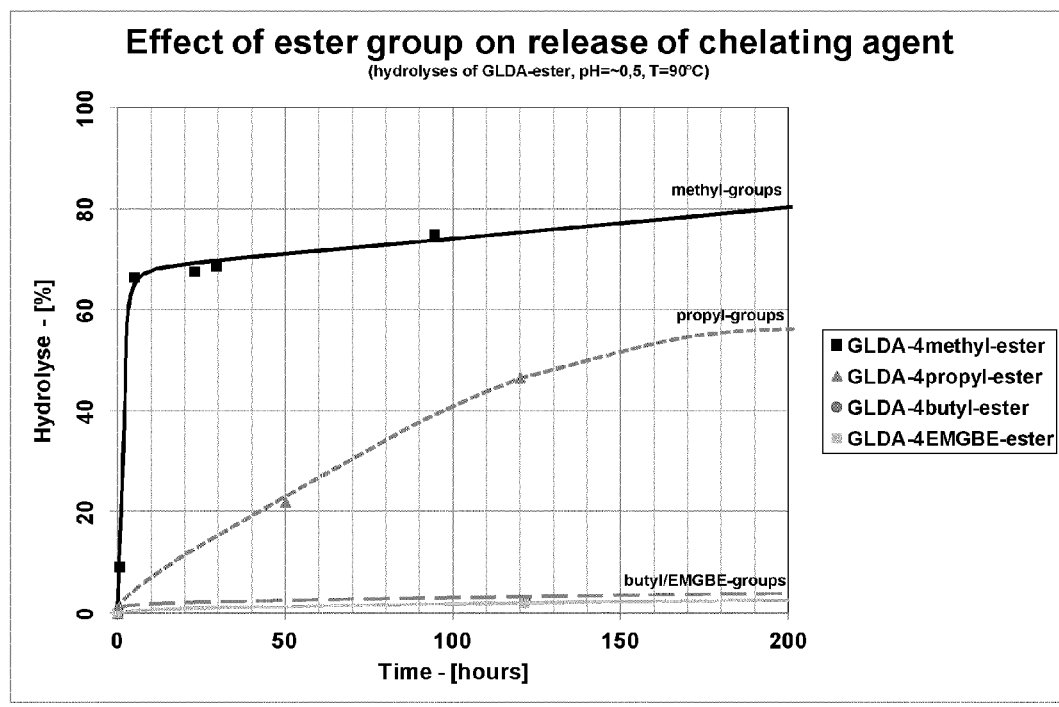

The release of GLDA is influenced by the length of the alcohol group, as is seen in FIG. 2. The longer the alcohol groups of the GLDA ester, the slower the rate of hydrolysis. The difference in hydrolysis rate clearly demonstrates that the release of GLDA acid and alcohol groups can be tailored to the needs of the well.

Example 3c

Comparison Between Methyl and Propyl Esters for GLDA vs EDTA

Figure 3:
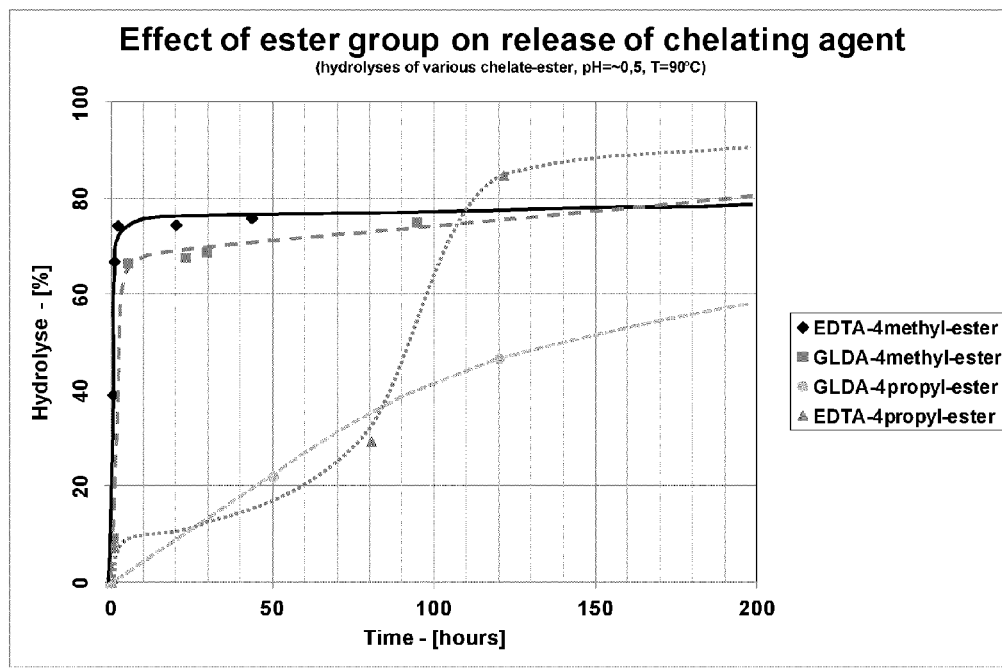

FIG. 3 gives a representation of the hydrolysis of the esters. As in Example 3 b the hydrolysis rate depends on the length of the alcohol group used to form the ester. It is worth noting that the EDTA esters hydrolyze faster than their GLDA ester counterparts. Even though initially there is no significant difference in the speed of hydrolysis, after ~3 days the speed of EDTA ester hydrolysis has increased considerably compared to that of GLDA ester hydrolysis.

Example 3d

Effect of pH

Figure 4:
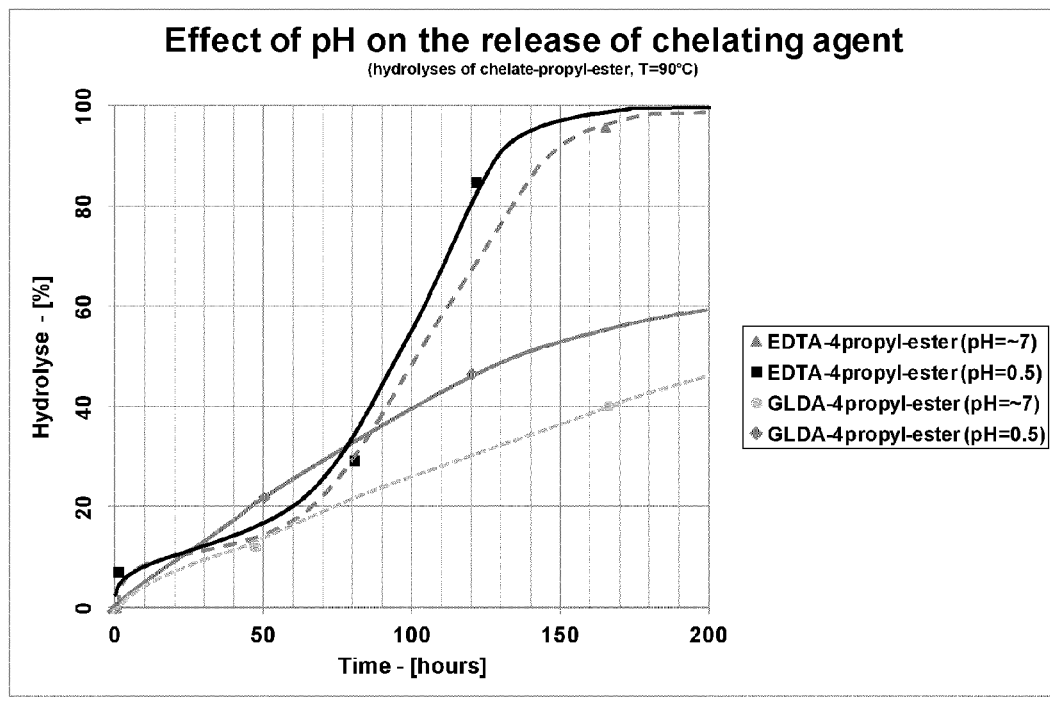

The esters synthesized via the thionyl chloride route are acidic because of the HCl salt that is formed during reaction. Consequently, the pH will be around ~1 when the esters are dissolved in water. Under downhole conditions the pH might be higher due to the interaction with other chemicals. To check the influence of the pH, samples were adjusted with caustic to a pH of 7. In FIG. 4 the effect of the pH on the release of chelating agent of GLDA/EDTA-propyl esters is demonstrated. The hydrolysis rate decreased slightly with increasing pH.

The invention claimed is:

1. Chelating agent precursor of the chelating agents glutamic acid N,N-diacetic acid (GLDA) and/or methylglycine N,N-diacetic acid (MGDA), wherein at least one of the carboxylic acid groups is present as a carboxylic acid derivative selected from the group consisting of anhydrides, esters, combinations thereof, and salts thereof, provided that it is not the triethyl ester of GLDA, the triethyl mono-t-butyl ester of GLDA, the tri-t-butyl ester of GLDA, the monobenzyl tri-t-butyl ester of GLDA, any ester that contains azacycloalkane groups, (S)-diethyl 2,2'-(1-benzyloxy)-1,5-dioxo-5-(prop-2-ynylamino)pentan-2-ylazanediyl-diacetate, diethyl 2,2'-(5-(3-azidopropylamino)-1-(benzyloxy)-1,5-dioxo-pentan-2-ylazanediyl-diacetate, the trimethyl ester of MGDA, the monomethyl ester dimethylamide of MGDA, the dibenzyl ester of MGDA, the dibenzyl mono t-butyl ester of MGDA, the di t-butyl ester of MGDA, the di-t-butyl-monobenzyl ester of MGDA, and esters of GLDA immobilized on a gel,
   wherein, when the carboxylic acid derivative is an ester, it is an ester of an alcohol selected from the group of aliphatic alcohols containing 1 to 12 carbon atoms that optionally may contain additional hydroxyl, amine and/or ether groups, and
   wherein, when the carboxylic acid derivative is an anhydride, it is an anhydride of a carboxylic acid selected from the group consisting of fatty acids and aliphatic carboxylic acids containing 1 to 12 carbon atoms that optionally may contain additional hydroxyl, amine, carboxylic acid and/or ether groups.

2. Fluid containing the chelating agent precursor of claim 1 and a liquid.

3. Fluid of claim 2, wherein the liquid is an aqueous liquid.

4. A method of using a chelating agent precursor of claim 1 that is selected from glutamic acid N,N-diacetic acid (GLDA) and/or methylglycine N,N-diacetic acid (MGDA) wherein at least one of the carboxylic acid groups is present as a carboxylic acid derivative selected from the group consisting of anhydrides, esters, combinations thereof, and salts thereof, or a fluid containing the chelating agent precursor and a liquid, in an application wherein delayed acidity or chelating capacity is useful, the method comprising using the chelating agent precursor for descaling, bleaching, cleaning, or treating oil and/or gas-containing subterranean formations.

5. The method of claim 4, wherein the carboxylic acid derivative is an ester from a C1-06 alcohol or a C1-C6 glycol that is used in treating a subterranean formation wherein the chelating agent precursor is at least partly hydrolyzed and the alcohol or glycol is released and assists in hydrate inhibition and/or acts as a mutual solvent.

6. Process to treat a subterranean formation wherein a chelating agent precursor of claim 1 that is selected from glutamic acid N,N-diacetic acid (GLDA) and/or methylglycine N,N-diacetic acid (MGDA), wherein at least one of the carboxylic acid groups is present as a carboxylic acid derivative selected from the group consisting of anhydrides, esters, combinations thereof, and salts thereof, or a fluid containing the chelating agent precursor, is introduced into the formation.

7. Process of claim 6, wherein the chelating agent precursor is at least partly hydrolyzed when it is introduced into the formation or thereafter.

8. Process of claim 7, wherein the fluid in addition contains an agent that assists in the hydrolysis of the chelating agent precursor to release GLDA and/or MGDA.

9. Process of claim 6, wherein the chelating agent precursor is an ester of GLDA.

10. Process of claim 9, wherein the chelating agent precursor is an ester of GLDA with a C1-C6 alcohol or a C1-C6 glycol.

11. Process of claim 6, wherein the pH of the fluid is between 1 and 7.

12. Process of claim 6, wherein the subterranean formation is contacted with the fluid at a temperature of between 25° C. and 204° C.

13. Process of claim 8, wherein the agent comprises an enzyme, a base or an acid.

* * * * *